US008119985B2

(12) United States Patent
Stewart et al.

(10) Patent No.: US 8,119,985 B2
(45) Date of Patent: *Feb. 21, 2012

(54) METHODS AND APPARATUS FOR STATISTICAL CHARACTERIZATION OF NANO-PARTICLES

(75) Inventors: Diane K. Stewart, Ipswich, MA (US); Daniel Rosenthal, Boxford, MA (US); Michel Epsztein, Lexington, MA (US)

(73) Assignee: FEI Company, Hillsboro, OR (US)

( * ) Notice: Subject to any disclaimer, the term of this patent is extended or adjusted under 35 U.S.C. 154(b) by 190 days.

This patent is subject to a terminal disclaimer.

(21) Appl. No.: 12/463,285

(22) Filed: May 8, 2009

(65) Prior Publication Data

US 2009/0326866 A1   Dec. 31, 2009

Related U.S. Application Data

(63) Continuation of application No. 11/481,574, filed on Jul. 6, 2006, now Pat. No. 7,544,938.

(60) Provisional application No. 60/697,343, filed on Jul. 7, 2005.

(51) Int. Cl.
  *G01N 23/05* (2006.01)

(52) U.S. Cl. ........ 250/310; 250/251; 250/306; 250/309; 250/311; 977/840; 977/842; 977/849; 977/880; 977/881

(58) Field of Classification Search ............ 850/62, 850/63; 250/306, 307, 309, 310, 311; 977/840, 977/842, 849, 880, 881
See application file for complete search history.

(56) References Cited

U.S. PATENT DOCUMENTS

| 5,981,962 | A | 11/1999 | Groves et al. |
|---|---|---|---|
| 5,986,264 | A * | 11/1999 | Grunewald ............... 250/310 |
| 6,306,610 | B1 * | 10/2001 | Bawendi et al. ............ 435/7.1 |
| 6,797,953 | B2 | 9/2004 | Gerlach et al. |
| 6,807,874 | B2 | 10/2004 | Totoki |
| 6,889,113 | B2 | 5/2005 | Tasker et al. |
| 6,986,280 | B2 | 1/2006 | Muchenhirm |
| 7,090,783 | B1 * | 8/2006 | Cui et al. .................. 216/40 |
| 7,110,585 | B2 * | 9/2006 | Cork et al. ................ 382/128 |
| 7,544,938 | B1 * | 6/2009 | Stewart et al. ............ 250/310 |
| 7,712,874 | B2 | 5/2010 | Nishio et al. |
| 2003/0168594 | A1 | 9/2003 | Muckenhirn |

(Continued)

FOREIGN PATENT DOCUMENTS

JP   2004-301768   10/2004

(Continued)

OTHER PUBLICATIONS

Griffith, Saul et al. "Nanostructure fabrication by direct electron-beam writing of nanoparticles," J. Vac. Sci. Technol., Nov./Dec. 2002, pp. 2768-2772, B 20(6).

(Continued)

*Primary Examiner* — Robert Kim
*Assistant Examiner* — Nicole Ippolito
(74) *Attorney, Agent, or Firm* — Scheinberg & Griner, LLP; Michael O. Scheinberg; Robert Amedeo

(57) ABSTRACT

A method and apparatus for determining statistical characteristics of nano-particles includes distributing the nano-particles over a surface and then determining properties of the nano-particles by automatic measurement of multiple particles or by a measurement that determines properties of multiple particles at one time, without manipulating individual nano-particles.

21 Claims, 4 Drawing Sheets

U.S. PATENT DOCUMENTS

| | | | |
|---|---|---|---|
| 2004/0033679 A1* | 2/2004 | Jacobson et al. | 438/510 |
| 2005/0023434 A1* | 2/2005 | Yacoubian | 250/200 |
| 2006/0093749 A1* | 5/2006 | Kim et al. | 427/458 |
| 2007/0009405 A1* | 1/2007 | Hatakeyama et al. | 422/186.04 |
| 2007/0284544 A1* | 12/2007 | Ishihara et al. | 250/492.1 |
| 2008/0102114 A1* | 5/2008 | Koritala et al. | 424/456 |

FOREIGN PATENT DOCUMENTS

| | | |
|---|---|---|
| JP | 4200373 | 10/2008 |
| WO | 9848443 | 10/1998 |

OTHER PUBLICATIONS

Nohmi, Takashi et al. "Electrospray Mass Spectrometry of Poly(ethylene glycols) with Molecular Weights up to Five Million," J. Am. Chem. Soc., 1992, pp. 3241-3246, vol. 114.

Fenn, John B., et al. "Electrospray Ionization for Mass Spectrometry of Large Biomolecules," J. Am. Chem., Oct. 1989, pp. 64-71, vol. 246.

Kong, David S. et al. "Conductive Nanostructure Fabrication by focused ion beam direct-writing of silver nanoparticles," J. Vac. Sci. Technol., Nov./Dec. 2004, pp. 2987-2991, B 22(6).

Wilhelm, Eric J. et al. "Nanoparticle-based microelectromechanical systems fabricated on plastic," Applied Physics Letters, Dec. 2004, pp. 6424-6426, vol. 85 No. 26.

Wilhelm, Eric J. et al. "Direct printing of nanoparticles and spin-on glasses by offset liquid embossing," Applied Physics Letters, May 2004, pp. 3507-3509, vol. 84, No. 18.

Ridley, Brent A. "All-Inorganic Field Effect Transistors Fabricated by Printing," Science, Oct. 1999, pp. 746-749, vol. 286.

Whitehouse, Craig et al. "Electrospray Interface for Liquid Chromatographs and Mass Spectrometers," Anal. Chem., 1985, pp. 675-679, vol. 57.

\* cited by examiner

```
┌──────────────────────┐      ┌──────────────────────┐
│ Form charge pattern  │─102  │ Load nano-particles  │─104
│    on substrate      │      │  into spray apparatus│
└──────────┬───────────┘      └──────────┬───────────┘
           │                             │
           └──────────────┬──────────────┘
                          ▼
              ┌──────────────────────┐
              │  Spray Nano-particles│─106
              │    onto substrate    │
              └──────────┬───────────┘
                         ▼
              ┌ ─ ─ ─ ─ ─ ─ ─ ─ ─ ─ ─┐
              │Purge excess nano-    │─108
              │ particles from       │
              │    substrate         │
              └ ─ ─ ─ ─ ┬ ─ ─ ─ ─ ─ ─┘
                        ▼
              ┌ ─ ─ ─ ─ ─ ─ ─ ─ ─ ─ ─┐
              │Coat substrate with   │─110
              │conductive material   │
              │   for charge control │
              └ ─ ─ ─ ─ ┬ ─ ─ ─ ─ ─ ─┘
                       ▼
              ┌──────────────────────┐
              │ Form representation  │─114
              │   of nano-particles  │
              └──────────┬───────────┘
                         ▼
              ┌──────────────────────┐
              │ Analyze representation│─116
              │   of nano-particles   │
              └──────────┬───────────┘
                         ▼
              ┌ ─ ─ ─ ─ ─ ─ ─ ─ ─ ─ ─┐
              │High resolution image │─120
              │ of individual        │
              │   nano-particles     │
              └ ─ ─ ─ ─ ─ ─ ─ ─ ─ ─ ─┘
```

FIG. 1

METHODS AND APPARATUS FOR STATISTICAL CHARACTERIZATION OF NANO-PARTICLES

This application is a continuation of and claims priority from U.S. application Ser. No. 11/481, 574 filed on Jul. 6, 2006, which claims priority from U.S. Provisional Application No. 60/697,343 filed on Jul. 7, 2005, both of which are incorporated herein by reference.

TECHNICAL FIELD OF THE INVENTION

The present invention relates to measuring small particles, and in particular, to characterizing populations of nano-particles.

BACKGROUND OF THE INVENTION

Researchers are finding a large number of potential applications for nano-particles in diverse field. For example, there is considerable interest in using nano-particles, particularly carbon structures, for medical applications, in batteries and fuel cells, and as coatings with desirable mechanical, thermal, electromagnetic, and/or optical properties, and for use in drilling and industrial polishing. Such carbon structures include, for example, carbon nano-tubes ("CNT"), and fullerenes, also known as "bucky balls," such as C-60, C70, C76, and C84.

Nano-particles could be used as a component of a drug delivery system to deliver a drug, radiation, or other therapeutic agent to a targeted part of the body. For these applications the size of the nano-particles is critical. Because applications that use nano-particles typically use large quantities of nano-particles, it is important to be able to characterize large groups, that is, populations of nano-particles.

While there are many known methods to manufacture CNTs, such as combustion methods and arc methods, it has been difficult to characterize the results of the manufacturing process to determine the size and other properties of the product of the manufacture. Current methods entail sampling and manually measuring individual nano-particles, for example, using a scanning electron microscope (SEM) or atomic force microscope (AFM). Such manual methods are slow and expensive, and are in fact economically prohibitive to commercial success of these technologies. Without an efficient way to characterize populations of nano-particles, it is difficult to control the manufacturing process to consistently produce the desired results. Moreover, statistical quality control will be required for almost any application of nano-particles, and is particularly important in medical applications, such as drug delivery systems. Without an efficient way to characterize populations of nano-particles, their practical applications will be limited.

SUMMARY OF THE INVENTION

An object of the invention is to provide a method and apparatus to statistically characterize populations of nano-particles.

In a preferred embodiment, a number of particles, as individuals or in small groups, are spread on a surface. The particles are then characterized by an analytical instrument. By spreading the particles, instruments can efficiently analyze multiple particles without having to manipulate individual particles.

In a preferred embodiment, electrical, chemical, or other properties of the nano-particles are used to distribute the nano-particles on a surface. In one embodiment, the surface is prepared by forming a pattern of electrical charges on the surface. The particles can be ionized and the particles are arrayed on the surface in a pattern determined by the charge pattern and the electrical properties, such as the net charge, on the nano-particles.

The particles are then characterized, for example, using an instrument that measures individual particles, such an electron microscope, along with automated pattern recognition software, that can find and characterize the individual nano-particles. Another way of characterizing the nano-particles is to use an instrument, such as a scatterometer, that characterizes the nano-particles spread on the surface, without measuring individual particles. Another method uses projection illumination whereby a broad beam of electrons is applied to the particles, and the resulting secondary or backscatter electrons are focused onto a two dimensional electron sensor array. An image is reconstructed and then analyzed, thereby avoiding single scans of individual particles.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes as the present invention. It should also be realized by those skilled in the art that such equivalent constructions do not depart from the spirit and scope of the invention as set forth in the appended claims.

BRIEF DESCRIPTION OF THE DRAWINGS

For a more through understanding of the present invention, and advantages thereof, reference is now made to the following descriptions taken in conjunction with the accompanying drawings, in which:

FIG. 1 is a flow chart showing the steps of a preferred embodiment of the invention.

DETAILED DESCRIPTION OF PREFERRED EMBODIMENTS

Figure 2:
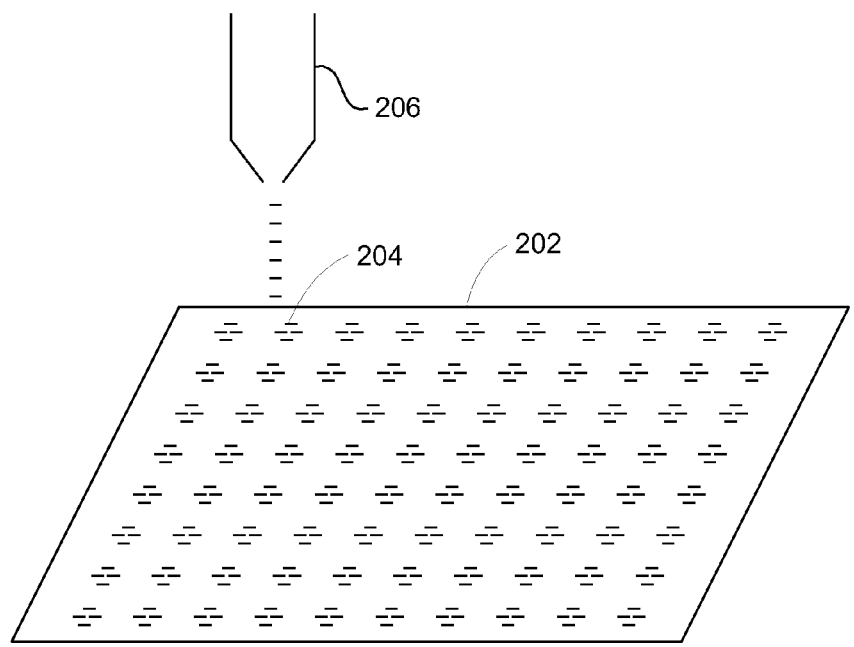
FIG. 2 shows forming a charge pattern on a surface in accordance with a preferred embodiment of the invention.

A preferred embodiment spreads a large number of nano-particles onto a surface, and then characterizes the nano-particles to determine statistics describing the population. Because the particles are spread, it is easier to measure the particles and unnecessary to manipulate individual particles for measurement. In some embodiments, the particles can be distributed by forming force centers on the surface, the force centers being areas that interact with the nano-particles to attract or repel them. The force centers can be, for example, groups of electrical charges that attract or repel ionized or polar nano-particles or chemicals that attract or repel the nano-particles or coatings on the nano-particles.

Depending on the instruments used for characterization, the characterization of the particles could include, for example, dimensions, chemical composition, electrical properties, optical properties, or any other property. Any statistics could be determined from any of the properties. For example, the statistical distribution of a characteristic could be determined, including the mean, standard deviation, minimum, maximum, skew, kertosis, and other properties. The number of particles measured, either individually or as part of an overall measurement, to determine the statistics is typically greater than 25, greater than 50, greater than 100, or greater than 200. There is no upper limit to the number of nano-particles used in the characterization. Nano-particle, as the term is used herein, refers to particles that are smaller than 1000 μm, smaller than 100 μm, smaller than 10 μm, or smaller than 1 μm.

In some embodiments, the nano-particles are distributed in a deterministic pattern, that is, in a pattern determined by electrical charges or other force centers formed on a surface, to facilitate characterization. In some embodiment, the nano-particles may be spread in a random pattern for characterization.

In some embodiments, the particles are aligned relative to each other or to a reference direction to facilitate ease or accuracy of measurement. For example, carbon nano-tubes could be aligned so that the long dimension of individual particles are perpendicular to an electron microscope scan direction, with one end of all the individuals aligned to a reference line, thus facilitating measurement. The particles may be aligned by shaping the charge pattern, for example, by using continuous or discontinuous lines of charge, instead of dots of charge.

In some embodiments, the particles are distributed by ionizing the particles, forming a charge pattern on the surface, and then spraying the ionized particles onto the surface, with the charge pattern determining the distribution of the particles. In other embodiments, the particles may not require an ionizing step. In some embodiments, charged or uncharged particles can be randomly spread on the surface, without using a charge pattern. In some embodiments, the repulsion among particles can be used to distribute the particles. In some embodiments, dipole moments of the charges are used, instead of ionization. In other embodiments, chemical or other forces are used to determine the nano-particles pattern.

FIG. 1 shows the steps of a preferred embodiment. In step 102, a charged pattern is formed on a substrate. FIG. 2 shows a substrate 202 having a pattern of negative charges 204 formed thereon. A pattern of positive charges could also be used, or a pattern of mixed positive and negative charges. FIG. 2 shows that the charges can be deposited by a charged particle beam system, such by an electron beam column 206 or other charged particle beam, such as a focused ion beam. The charge pattern can also be formed using a laser beam, as is a photocopy process. If a charged particle beam is used to form the charge pattern, the operation of forming the charge pattern is typically performed in a vacuum. Subsequent steps, such as spreading the nano-particles onto the charge pattern, may be performed in a vacuum, or in air.

Figure 3:
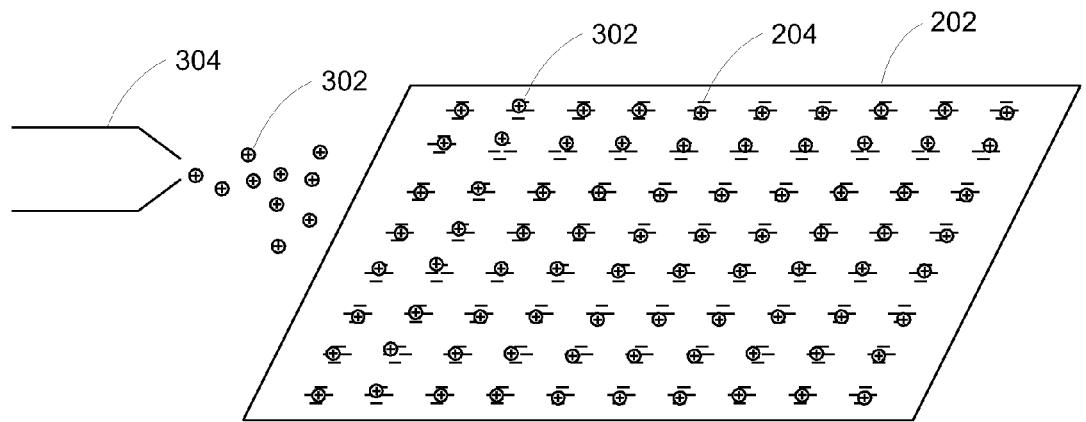
FIG. 3 shows nano-particles being sprayed over the charged distribution of FIG. 2.

In step 104, the nano-particles 302 are loaded into a spray apparatus 304 shown in FIG. 3. In step 106, the nano-particles are sprayed onto the substrate. FIG. 3 shows positive nano-particles 306 arranged on the pattern of negative charges on the substrate.

The charge pattern determines the arrangement of the nano-particles on the substrate. For example, if the nano-particles are positively charged, they will be attracted to the negative charges on the substrate. If the nano-particles are negatively charged, they will be repelled from the negative charges on the substrate. The dipole moment of some neutral nano-particles will cause them to also be attracted to the charged areas. In optional step 108, the substrate may be purged, for example, by the passage of a gas and optionally using ultrasound, to remove excess nano-particles. In optional step 110, the sample may be coated with a substance for the purpose of charge control through a chemical or beam-induced chemistry process. At this point the substrate will have a pre-determined number of nano-particles arranged in a deterministic pattern and alignment with favorable charging characteristics.

Figure 4:
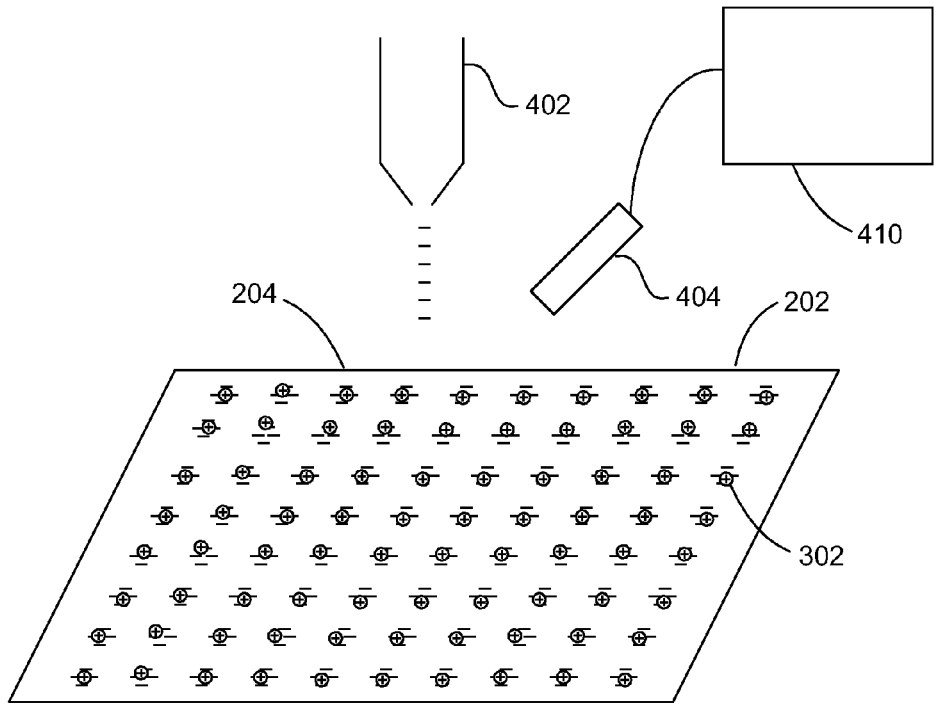
FIG. 4 shows the nano-particles of FIG. 3 being characterized by an electron microscope.

In step 114, a representation of the nano-particles is obtained. For example, the representation may be an SEM image or a scatterometer graph. In one embodiment, the substrate and the nano-particles may be imaged using an SEM, possibly with multiple scans with complimentary imaging parameters. FIG. 4 shows an SEM including an electron column 402 and a detector 404 for detecting secondary or backscattered electrons. The detector is used to form a representation of the nano-particles, such as an SEM image. Alternatively, projection illumination and focusing of secondary electrons or backscattered electrons onto a two dimensional sensor may be used. Alternatively, an integrating measurement, such as scatterometer, may be used. The invention is not limited to any particular type of instrument for characterizing the nano-particles.

Figure 5:
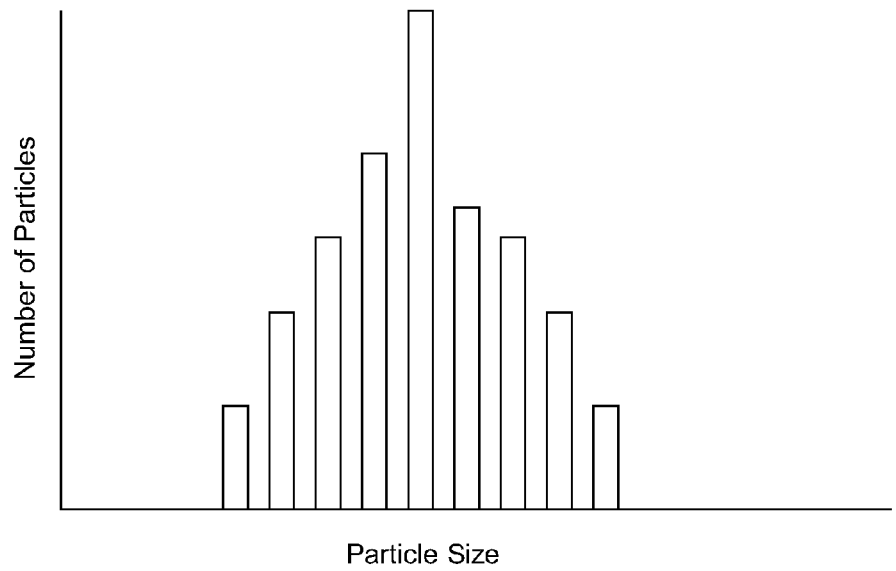
FIG. 5 shows a statistical distribution of a characteristic of the nano-particles measured as shown in FIG. 4.

In step 116, the representation is analyzed. For example, if the representation is an SEM image or images, the image or images can be analyzed using optical recognition software. A computer 410 forms an image from signals from detector 404, and software running on computer 410 or another computer locates and measures dimensions of the nano-particles. Statistics, such as the histogram of FIG. 5, can then be generated from the measurements. The use of automated image recognition software allows a large number of nano-particles to be measured with little or no human intervention, after the system is set up and trained what to look for and how to measure. The distribution of the nano-particles over the substrate facilitates the use of automatic measurements. Optionally, in step 120 individual nano-particles can be singled out for high resolution imaging, and visual display of critical dimensions.

U.S. Pub. Pat. App. No. 2004/0033679, which is hereby incorporated by reference, describes a method of patterning of nanostructures by forming a charge pattern on a substrate, and then distributing nano-particles onto the substrate. An energy beam, such as an electron beam, ion beam, or laser, is used to apply a charge pattern to a substrate, such as an insulating sheet of mylar, poly(methylmethacrylate), $SiO_2$, or $CaTiO_3$. For example, an electron beam can be used to deposit negative charges as shown in FIG. 2, or an ion beam can be used to deposit positive or negative charges. Alternatively, in a process similar to laser printing, a photoconductive substrate can be charged, and then a pattern formed by discharging the substrate using a laser.

For charging a large surface with a high throughput of many particles, multiple sites could be charged simultaneously using parallel illumination by multiple charged particle beams. For example U.S. Pat. No. 6,797,953 describes a system using multiple electron beam columns to produce multiple electron beams. Other known multiple beam systems includes those described in WO98/48443 and U.S. Pat. No. 5,981,962. Another method for rapidly forming a charge pattern on a surface includes flood projection of charged particles over a grid, which shields the surface, only allowing charged particle to reach the surface at desired locations. Another method of forming a charged surface is to use a substrate having electrical circuitry to allow the formation of charged surface areas by delivering charge through the circuitry or through a photoelectric effect, such as a pre-charged semiconductor substrate, such as a charged coupled device ("CCD").

Figure 6:
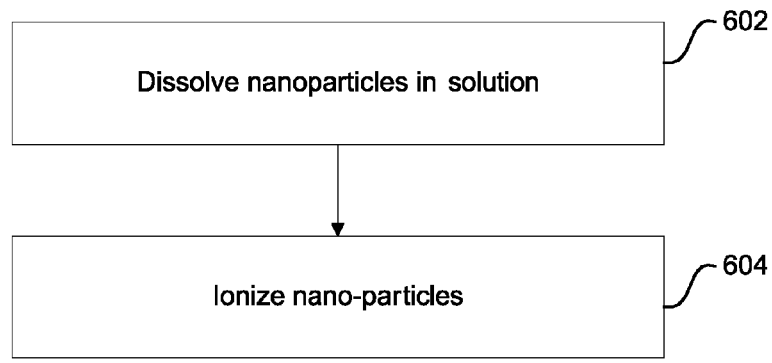
FIG. 6 is flowchart showing preferred steps for ionizing nano-particles.

After the charge pattern is formed, ionized nano-particles are sprayed over the charge pattern. The nano-particles can be ionized by using a spray ionization technique, such as electrospray ionization, which is described, for example, by Fenn et al. "Electrospray Ionization For Mass Spectrometry Of Large Biomolecules," Science, vol. 246, pp 64-70 (1989) ("Fenn"). As shown in FIG. 6, the nano-particles are in a solvent in step 602. The nano-particles are ionized in step 604 in the electrospray apparatus.

Figure 7:
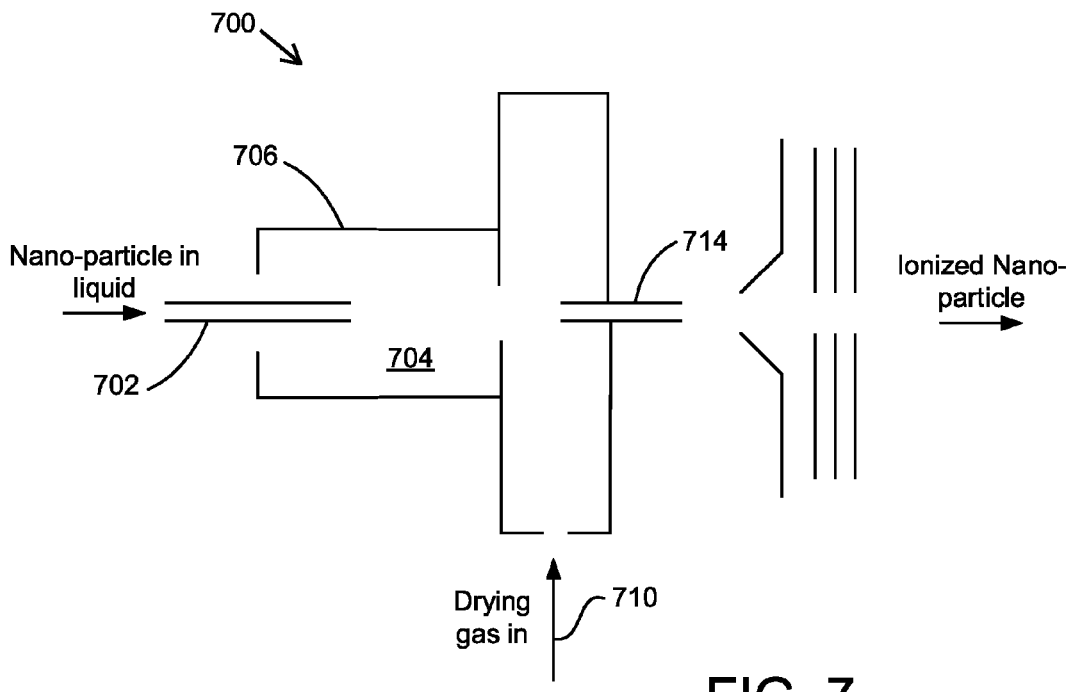
FIG. 7 shows part of an apparatus for ionizing nano-particles and spraying the charged nano-particles onto a surface.

FIG. 7 shows schematically a spray ionization device as described in Fenn. The apparatus is described in detail in C. M. Whitehouse et al., Analytical Chemistry, 57:675 (1985). The apparatus 700 includes a stainless steel hypodermic needle 702 through which a sample solution enters the ES chamber 704 at flow rates typically between 1 μl/min and 20 μl/min. The needle is typically maintained at a few kilovolts relative to the walls of the chamber. The surrounding cylindrical electrode 706 helps shape the distribution of potential and direct the flow 710 of the bath gas. The resulting field at the needle tip charges the surface of the emerging liquid, dispersing it by Coulomb forces into a fine spray of charged droplets. The droplets migrate toward the inlet end of a glass capillary 714 at the end wall of the chamber 704. A flow of a drying gas, typically at a pressure of about 800 torr, an initial temperature from 320 K to 350 K, and a flow rate of about 100 ml/s facilitates evaporation of solvent from each droplet, decreasing its diameter as it drifts toward the end wall of the chamber 704 under the influence of the electric field. The parameters used for any specific nano-particles can be determined by skilled persons without undue experimentation following the guidance provided herein and by the published literature, such as the articles cited above.

It is thought that the charge density on the surface of the emerging liquid increases until the Coulomb repulsion approximates the surface tension, at which time the droplet breaks apart, producing charged daughter droplets that also evaporate. This sequence of events repeats until the radius of curvature of a daughter droplet becomes small enough that the field due to the surface charge density is strong enough to desorb the ionized nano-particle from the droplet into the ambient gas. The desorbing ions include cations (or anions), to which are attached solvent or solute species that are not themselves ions, thus producing so-called "quasi-molecular" ions.

For an embodiment in which the nano-particles to be characterized are carbon structures, such as CNT or fullerenes, a preferred substrate is a quartz plate. The charge spots are preferably as small as the charge-producing beam will produce. In some embodiments, the spots can be relatively close together. The spacing between charged spots can be different in different directions, and the spots themselves can be symmetrical or unsymmetrical. For example, for nano-particles that have a long dimension, the charged spots can be arranged to create rows of particles arranged end to end, the particles contacting each other, or not, depending on the embodiment, with spacing between the rows. In preferred embodiments, electrospray ionization as described above is used. The CNTs are held in suspension of a liquid preferably one having a high vapor pressure, such as a solvent like acetone or ethanol. As the solvent evaporates and the droplets become smaller, the particle CNT becomes unstable within the drop as the charge concentration increases, until the ionized CNT comes out of suspension. Other methods of ionizing the CNT can also be used, for example, plasma desorption, fast ion (or atom) bombardment, laser desorption, field desorption, electrohydrodynamic, or other spray ionization methods, such as thermospray or aerospray.

In some embodiments, the nano-particles can be coated prior to spraying to facilitate ionization or to provide a coating that is attracted or repelled from the force centers on the substrate.

It is possible that the as-deposited nano-particles may not assemble in a dense enough assembly due to electrostatic forces on the substrate and within the population. If this occurs it may be necessary to manipulate the electrostatic forces with potentials on in situ surfaces such as structures that have been previously created on the surface using lithography, for example.

Charged CNTs leaving the electrospray apparatus are sprayed onto the charge-patterned substrate as described in U.S. Pub. Pat. App. No. 2004/0033679. The CNTs are directed toward the charge pattern. The velocity of the particles in the vicinity of the charged pattern is preferably reduced to facilitate capture of the particles by the charged surface. The velocity of the charged particles can be controlled using an electric field, a magnetic field, or a combination of the two as described in U.S. Pub. Pat. App. No. 2004/0033679 to increase the probability of the particles adhering to the charge pattern. The number of nano-particles introduced into the region around the substrate can be controlled by using a nano-particle counting scheme, similar to a channeltron ion detector, to determine the number of nano-particles per time coming from the nano-particle source.

After the CNTs are sprayed onto the pattern, the size or other properties of the nano-particles are evaluated. For example, the sizes can be determined using an electron microscope and pattern recognition software, available from Cognex Corporation. An operator can manually locate a nano-particle, and determine its size from the size of the image and knowledge of the magnification. The operator can then train the software to automatically recognize other nano-particles and automatically perform similar measurements. The software can perform a search algorithm to scan the entire substrate surface, locate nano-particles, and measure the particles found. Alternatively, the location of the charged areas of the substrate can be programmed into the software, and images taken and analyzed at those locations. A system for automatically imaging, measuring, and generating statistics is described, for example, in U.S. Pat. No. 6,889,113 for "Graphical Automated Machine Control and Metrology," which is assigned to the assignee of the present invention and which is hereby incorporated by reference.

Alternatively, a system that measures statistical characteristics or other properties without individual measurements can be used. For example, scatterometry is described, for example, in U.S. Pub. Pat. App. No. 2003/0168594 for an "Integrated Measuring Instrument," which is hereby incorporated by reference. Scatterometry generates a graph that depends upon the physical characteristics of a repetitive pattern. The graph is compared to library graphs generated from patterns with known parameters. A match between the graph of the unknown pattern and a library graph indicates that the unknown pattern has the same physical parameters, such as spacing, size, and composition, as the nano-particle pattern used to generate the matching library graph. For example, one can compile a library of scatterometry graphs for different sizes of single-walled CNTs distributed onto a specified charge pattern. To determine the characteristics of an unknown sample of a single-walled CNT, one could produce a scatterometry graph of the unknown single-walled CNT on the specified charge pattern and compares the graph with the library graphs. The size of the CNT in the sample will be the same as the size of the CNT in the matching library graph. Typical single wall CNTs are about 2-3 nm by 10+ nm.

By arranging nano-particles on a surface, embodiments of the invention facilitate rapid measurement and analysis of multiple particles. Optional coating of nano-particles to make them conductive can provide for better imaging and measurement. The particles can be coated before or after distributing the nano-particles onto the substrate. The invention permits the use of existing pattern recognition algorithms to locate and measure critical dimensions on these pre-arranged nano-particles.

A preferred embodiment provides the use of two dimensional statistical and spectral analyses to extract statistics from noisy or low resolution fast scan images of large numbers of samples.

The following apparatus and method of operation will allow for quickly extracting statistics of the physical sizes of large numbers of nano-particles.

A preferred embodiment includes:

A. A device for producing a charge pattern on a substrate, such as an integrated nano-particle spray apparatus, such as the MIT nano-spray described in U.S. Pub. Pat. App. No. 2004/0033679.

B. An integrated chemical delivery system for charging and delivering nano-particles (such as a system available from NanoChemiX).

C. An imaging or measuring instrument, for example, a small chamber SEM, such as those available from FEI Company, the assignee of the present application.

D. An integrated image analysis hardware and software (such as Cognex based system).

In place of C and D, some embodiments can use a measurement system that analyzes the surface, for example, determining spatial frequency spectra, without requiring a viewable image.

While electrical charges on the surface can be used as force centers to attract or repel the nano-particles to distribute them, the invention is not limited to the use of electrical force to distribute the nano-particles. In some other embodiment, for example, the distribution can be formed by functionalizing portions of the substrate. For example, chemical attraction, rather than electrical attraction, can be used. For example, it is known that gold atoms are attracted to thiols, that is, sulfhydryl groups or molecule containing those groups. Thiols can be distributed onto the substrate in a pattern, and gold coated nano-particles can be sprayed onto the surface. The gold-coated nano-particles will be attracted to the thiol.

The term "population" as used herein means any group comprising a large number of nano-particles, for example, more than 30, although typically well over 1,000. There is no upper limit to the number of nano-particles in a population, and some populations may have millions or more nano-particles. For quality and process control, it is important to characterize populations by either direct measurement of the entire population or by statistical sampling of the population, which still requires the characterization of a large number of nano-particles.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of determining properties of nano-particles, comprising:
    forming a charge pattern on a substrate;
    distributing nano-particles onto the charge pattern, the charge pattern causing the nano-particles to spread across the surface of the substrate; and
    measuring a property of a plurality of nano-particles to determine statistical characteristics of the nano-particle population by:
    forming an image of the nano-particle population on the substrate; and
    using automated pattern recognition software to find and characterize the nano-particles in which measuring a property of a plurality of nano-particles to determine statistical characteristics of the nano-particle population includes measuring more than 25 nano-particles.

2. The method of claim 1 in which forming a charge pattern on a substrate includes directing a charged particle beam toward an insulating substrate.

3. The method of claim 1 in which distributing nano-particles onto the charge pattern includes distributing carbon containing molecules onto the charged pattern, the carbon containing molecules having a molecular weight greater than 720.

4. The method of claim 1 in which distributing nano-particles onto the charge pattern includes distributing fullerenes or carbon nanotubes.

5. The method of claim 1 in which distributing nano-particles onto the charge pattern includes ionizing the nano-particles.

6. The method of claim 5 in which ionizing the nano-particles includes mixing the nano-particles into a liquid and spraying the liquid through a nozzle into a drying gas.

7. The method of claim 1 further comprising coating the nano particles to facilitate measurement.

8. The method of claim 1 in which forming a charge pattern includes forming a pattern of chemicals on the surface.

9. A method of determining properties of nano-particles, comprising:
    forming a charge pattern on a substrate;
    distributing nano-particles onto the charge pattern, the charge pattern causing the nano-particles to spread across the surface of the substrate; and
    measuring a property of a plurality of nano-particles to determine statistical characteristics of the nano-particle population by:
    directing light at a specified angle onto the nano-particles on the substrate; and
    recording a pattern of the light scattered by the nano-particles while varying the wavelength of the incident light or by changing the specified angle of the incident light;

comparing the recorded pattern to reference patterns to determine a characteristic of the population of the nano-particles in which measuring a property of a plurality of nano-particles to determine statistical characteristics of the nano-particle population includes measuring more than 25 nano-particles.

10. The method of claim 9 in which measuring a property of a plurality of nano-particles to determine statistical characteristics of the nano-particle population includes measuring more than 50 nano-particles.

11. The method of claim 9 in which measuring a property of a plurality of nano-particles to determine statistical characteristics of the nano-particle population includes measuring more than 100 nano-particles.

12. The method of claim 9 in which forming a charge pattern on a substrate includes directing a charged particle beam toward an insulating substrate.

13. The method of claim 9 in which distributing nano-particles onto the charge pattern includes distributing carbon containing molecules onto the charged pattern, the carbon containing molecules having a molecular weight greater than 720.

14. The method of claim 9 in which distributing nano-particles onto the charge pattern includes distributing fullerenes or carbon nanotubes.

15. The method of claim 9 in which distributing nano-particles onto the charge pattern includes ionizing the nano-particles.

16. The method of claim 15 in which ionizing the nano-particles includes mixing the nano-particles into a liquid and spraying the liquid through a nozzle into a drying gas.

17. The method of claim 9 further comprising coating the nano particles to facilitate measurement.

18. The method of claim 9 in which forming a charge pattern includes forming a pattern of chemicals on the surface.

19. A method of determining properties of nano-particles, comprising:
forming a charge pattern on a substrate;
applying a plurality of nano-particles onto the charge pattern, the charge pattern causing the plurality of nano-particles to spread across the surface of the substrate;
creating a representation of the nano-particles; and
analyzing the representation of the plurality of nano-particles to determine statistical information of a nano-particle population by using pattern recognition software on a machine-readable medium executing on a machine in which measuring a property of a plurality of nano-particles to determine statistical characteristics of the nano-particle population includes measuring more than 25 nano-particles.

20. A method of characterizing a nano-particle population, comprising
forming a charge pattern on a substrate;
spraying nano-particles onto the substrate, the charge pattern causing the nano-particles to spread across the substrate;
creating a scanning electron microscope image representation of the nano-particles on the substrate;
analyzing the image to determine statistical information of the nano-particle population, wherein analyzing is performed by automated pattern recognition software on a machine readable medium executing on a machine in which measuring a property of a plurality of nano-particles to determine statistical characteristics of the nano-particle population includes measuring more than 25 nano-particles.

21. A method of characterizing a nano-particle population, comprising
forming a charge pattern on a substrate;
spraying nano-particles onto the substrate, the charge pattern causing the nano-particles to spread across the substrate so that the nano-particles can be analyzed without manipulating individual nano-particles;
creating a scatterometry graph representation of the nano-particles on the substrate;
analyzing the graph to determine statistical information of the nano-particle population by comparing the graph to library graphs generated from patterns with known parameters in which measuring a property of a plurality of nano-particles to determine statistical characteristics of the nano-particle population includes measuring more than 25 nano-particles.

* * * * *